US008939583B2

(12) United States Patent
Borycki et al.

(10) Patent No.: US 8,939,583 B2
(45) Date of Patent: Jan. 27, 2015

(54) OPHTHALMIC APPARATUS, METHOD OF CONTROLLING OPHTHALMIC APPARATUS AND STORAGE MEDIUM

(71) Applicant: Canon Kabushiki Kaisha, Tokyo (JP)

(72) Inventors: Dawid Borycki, Toruń (PL); Hiroshi Aoki, Saitama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/967,320

(22) Filed: Aug. 14, 2013

(65) Prior Publication Data

US 2014/0063460 A1 Mar. 6, 2014

(30) Foreign Application Priority Data

Aug. 30, 2012 (JP) ................................. 2012-190617

(51) Int. Cl.
*A61B 3/14* (2006.01)
*A61B 3/10* (2006.01)
*A61B 3/00* (2006.01)

(52) U.S. Cl.
USPC ............................ 351/208; 351/221; 351/246

(58) Field of Classification Search
USPC ................................................. 351/200–246
See application file for complete search history.

(56) References Cited

U.S. PATENT DOCUMENTS

| 8,506,082 B2* | 8/2013 | Saito ............................. 351/221 |
| 2007/0002277 A1* | 1/2007 | Hanebuchi .................... 351/206 |
| 2011/0058029 A1 | 3/2011 | Nakajima et al. |
| 2012/0140172 A1* | 6/2012 | Torii et al. ..................... 351/206 |
| 2012/0154746 A1* | 6/2012 | Nozato ......................... 351/205 |

FOREIGN PATENT DOCUMENTS

| JP | 2005-087608 A | 4/2005 |
| JP | 2008-029467 A | 2/2008 |
| JP | 2012-030054 A | 2/2012 |
| WO | 2006/105903 A | 10/2006 |
| WO | 2007/084748 A | 7/2007 |
| WO | 2011-158766 A | 12/2011 |

OTHER PUBLICATIONS

Foracchia et al., "Luminosity and Contrast Normalization in Retinal Images", Medical Image Analysis 9 (2005), pp. 179-190, November.
European Search Report issued in corresponding application No. 13180774.5 on Nov. 29, 2013.

* cited by examiner

*Primary Examiner* — Mohammed Hasan
(74) *Attorney, Agent, or Firm* — Carter, DeLuca, Farrell & Schmidt, LLP

(57) ABSTRACT

An ophthalmic apparatus comprising: an acquisition unit configured to acquire a first fundus image of an eye and a second fundus image of the eye; a first generation unit configured to generate, by performing processing of enhancing contrast of a first characteristic region of a part of the first fundus image, an image which corresponds to the first characteristic region; a second generation unit configured to generate, by performing processing of enhancing contrast of a second characteristic region of a part of the second fundus image which corresponds to the first characteristic region, an image which corresponds to the second characteristic region; and a correction unit configured to correct an acquisition position of a tomographic image of the eye based on a positional displacement between the images which respectively correspond to the first and second characteristic regions.

13 Claims, 5 Drawing Sheets

OPHTHALMIC APPARATUS, METHOD OF CONTROLLING OPHTHALMIC APPARATUS AND STORAGE MEDIUM

BACKGROUND OF THE INVENTION

1. Field of the Invention

The present invention relates to an ophthalmic apparatus, a method of controlling the ophthalmic apparatus, and a storage medium and, more particularly, to a technique for improving the accuracy of fundus tracking.

2. Description of the Related Art

Currently, an optical coherence tomography apparatus based on OCT (Optical Coherence Tomography) using multiwavelength light wave coherence is known. For example, this apparatus is used in an endoscope to obtain organ information and used in an ophthalmic apparatus to obtain retina information, thus expanding the field of application to the human body. The optical coherence tomography apparatus applied to the eyes is therefore becoming indispensable to outpatient clinics specialized in retinas as an ophthalmic apparatus.

Such an optical coherence tomography apparatus irradiates a sample with measurement light which is low-coherent light, and can measure backscattered light from the sample by using an interference system. This apparatus can obtain image information in the depth direction at a given point on the sample by irradiating the point on the sample with measurement light. The apparatus can also obtain a tomographic image of the sample by performing measurement while scanning measurement light on the sample. When being applied to the fundus, the apparatus can capture a tomographic image of the fundus of the eye to be examined at high resolution by scanning measurement light on the fundus of the eye to be examined, and hence has been widely used for ophthalmic care and the like for the retina.

Optical coherence tomography apparatuses generally use an imaging method of obtaining a plurality of tomographic images by iteratively scanning the fundus as a measurement target, in the horizontal or vertical direction. For example, an optical coherence tomography apparatus can obtain one fundus tomographic image with high image quality by acquiring a plurality of fundus tomographic images of the same region by scanning the same place on the fundus a plurality of times and averaging them. This apparatus can also obtain a three-dimensional image of the fundus by scanning the fundus a plurality of times while translating the scan position. When, however, performing such scanning a plurality of times, the apparatus requires a certain period of time to complete the entire imaging operation. For this reason, the eye may move during the scanning.

In contrast to this, the ophthalmic imaging apparatus disclosed in Japanese Patent Laid-Open No. 2008-29467 uses a method (to be referred to as "fundus tracking" hereinafter) of sequentially capturing front images of the eye to be examined, detecting the movement of the eye by using a plurality of obtained front images, and correcting the scan position in accordance with the detected movement of the eye. As described above, the optical coherence tomography apparatus places importance on the processing of reducing the influence of the movement of the eye to be examined.

In order to obtain a fundus tomographic image with high accuracy at high speed, the optical coherence tomography apparatus disclosed in Japanese Patent Laid-open No. 2012-30054 generates a reference image (to be referred to as a "template" hereinafter) by selecting a fundus observation image serving as a reference from which a feature point as an index of the movement of the eye to be examined has been extracted, generates another template using a fundus observation image of a fundus tracking target which is obtained after the generation of the template, and performs fundus tracking by template matching using the same feature point.

Assume that the eye to be examined has moved during capturing of an image serving as a fundus tracking target. In this case, vignetting or the like at the pupil of the eye may cause illuminance unevenness on the image. At this time, the contrast decreases at a feature point, in particular, at a characteristic region such as a blood vessel region, in the template of the image as the fundus tracking target. This may cause errors in the detection accuracy of template matching. As a result, an error in the scan position due to fundus tracking will cause displacement (distortion) on an acquired tomographic image. This distortion on the tomographic image may hinder image diagnosis by the doctor and also may make him/her mistake the distortion on the tomographic image for a morbid, portion. This may lead to misdiagnosis.

SUMMARY OF THE INVENTION

In consideration of the above problems, the present invention provides a technique which enables more accurate fundus tracking.

According to one aspect of the present invention, there is provided an ophthalmic apparatus comprising: a fundus image acquisition unit configured to acquire a first fundus image of an eye and a second fundus image of the eye which is captured at a time different from that of the first fundus image; a first generation unit configured to generate, by performing processing of enhancing contrast of a first characteristic region of a part of the first fundus image, an image which corresponds to the first characteristic region; a second generation unit configured to generate, by performing processing of enhancing contrast of a second characteristic region of a part of the second fundus image which corresponds to the first characteristic region, an image which corresponds to the second characteristic region; and a position correction unit configured to correct an acquisition position of a tomographic image of the eye based on a positional displacement between the image which corresponds to the first characteristic region and the image which corresponds to the second characteristic region.

According to one aspect of the present invention, there is provided a method of controlling an ophthalmic apparatus comprising the steps of: a fundus image acquisition step of acquiring a first fundus image of an eye and a second fundus image of the eye which is captured at a time different from that of the first fundus image; a first generation step of generating, by performing processing of enhancing contrast of a first characteristic region of a part of the first fundus image, an image which corresponds to the first characteristic region; a second generation step of generating, by performing processing of enhancing contrast of a second, characteristic region of a part of the second fundus image which corresponds to the first characteristic region, an image which corresponds to the second characteristic region; and a position correction step of correcting an acquisition position of a tomographic image of the eye based on a positional displacement between the image which corresponds to the first characteristic region and the image which corresponds to the second characteristic region.

Further features of the present invention will become apparent from the following description of exemplary embodiments with reference to the attached drawings).

DESCRIPTION OF THE EMBODIMENTS

An exemplary embodiment(s) of the present invention will now be described in detail with reference to the drawings. It should be noted that the relative arrangement of the components, the numerical expressions and numerical values set forth in these embodiments do not limit the scope of the present invention unless it is specifically stated otherwise.

First Embodiment

Schematic Arrangement of Optical Coherence Tomography Apparatus

The schematic arrangement of an optical coherence tomography apparatus (ophthalmic apparatus) according to the first embodiment will be described first with reference to FIG. 1. The optical coherence tomography apparatus acquires a tomographic image of the eye to be examined based on interference light obtained by interference between return light from the eye irradiated with measurement light through a scanning unit and reference light corresponding to the measurement light. The optical coherence tomography apparatus includes an optical head unit 100, a spectroscope 200, and a control unit 300. The arrangements of the optical head unit 100, spectroscope 200, and control unit 300 will be sequentially described below.

Arrangements of Optical Head Unit 100 and Spectroscope 200

The optical head unit 100 is formed from a measurement optical system for capturing two-dimensional and tomographic images of an anterior eye Ea or an eye E to be examined or a fundus Er of the eye. The internal arrangement of the optical head unit 100 will be described below. An objective lens 101-1 is placed to face the eye E. A first dichroic mirror 102 and a second dichroic mirror 103, which are arranged on the optical axis of the objective lens 101-1 and function as an optical path separation unit, separate the optical path. That is, the optical path is separated into a measurement optical path L1 of the OCT optical system, a fundus observation optical path/fixation lamp optical path L2, and an anterior eye observation optical path L3 for the respective wavelength bands.

The optical path L2 is caused to branch into optical paths to an APD (Avalanche PhotoDiode) 115 for fundus observation and to a fixation lamp 116 by a third dichroic mirror 118. In this case, reference numerals 101-2, 111, and 112 denote lenses. A focus lens driving unit such as a motor (not shown) drives the lens 111 (focus lens) to perform focus adjustment for the fixation lamp and for fundus observation. The APD 115 has sensitivity at the wavelength of fundus observation illumination light (not shown), more specifically, near 780 nm. The fixation lamp 116 emits visible light to make an eye to be examined hold visual fixation.

An X scanner 117-1 (for the main scanning direction) and a Y scanner 117-2 (for the sub-scanning direction perpendicular to the main scanning direction) are arranged on the optical path L2 to scan the light emitted from a fundus observation illumination light source (not shown) on the fundus Er of the eye E. The lens 101-2 is disposed such that its focal position is located near the central position between the X scanner 117-1 and the Y scanner 117-2. The X scanner 117-1 is formed from a resonant mirror. The X scanner 117-1 may be formed from a polygon mirror. A position near the central position between the X scanner 117-1 and the Y scanner 117-2 is optically conjugate to the position of the pupil of the eye E. The APD (Avalanche PhotoDiode) 115 is a single detector, and detects the light scattered/reflected by the fundus Er and returning from it. The third dichroic mirror 118 is a prism on which a perforated mirror or hollow mirror is deposited, and separates illumination light and return light from the fundus Er.

A lens 141 and an infrared CCD (charge coupled device) 142 for anterior eye observation are arranged on the optical path L3. The infrared CCD 142 has sensitivity at the wavelength of anterior eye observation illumination light (not shown), more specifically, near 970 nm. The optical path L1 is a component of the OCT optical system as described above, and is used to capture a tomographic image of the fundus Er of the eye to be examined. More specifically, this optical path is used to obtain an interference signal for the formation of a tomographic image.

A lens 101-3, a mirror 121, and an X scanner 122-1 and a Y scanner 122-2 which function as a scanning unit to scan light on the fundus Er of the eye to be examined are arranged on the optical path L1. In addition, the X scanner 122-1 and the Y scanner 122-2 are arranged such that a position near the central position between the X scanner 122-1 and the Y scanner 122-2 coincide with the focal position of the lens 101-3. Furthermore, the position near the central position between the X scanner 122-1 and the Y scanner 122-2 is optically conjugate to the position of the pupil of the eye E. With this arrangement, the optical path including the scanning unit as an object point becomes almost parallel between the lens 101-1 and the lens 101-3. This makes it possible to make the incident angle of light on the first dichroic mirror 102 equal to that on the second dichroic mirror 103 even if the X scanner 122-1 and the Y scanner 122-2 perform scanning.

A measurement light source 130 is also a light source for making measurement light enter the measurement optical path. In this embodiment, the measurement light source 130 is a fiber end, and has an optically conjugate relationship with the fundus Er of the eye E. Reference numerals 123 and 124 denote lenses. Of these lenses, the lens 123 (focus lens) is driven by a focus lens driving unit, such as a motor (not shown) to perform focus adjustment. Focus adjustment is performed to form the light emitted from the measurement light source 130 as the fiber end into an image on the fundus Er. The lens 123 functioning as a focus adjusting unit is placed between the measurement light source 130 and the X scanner 122-1 and the Y scanner 122-2 which function as the scanning unit. This makes it unnecessary to move either the lens 101-3 having a larger size than the lens 123, or an optical fiber 125-2.

This focus adjustment can form an image of the measurement light source 130 on the fundus Er of the eye E and also can cause return light from the fundus Er of the eye E to efficiently return to the optical fiber 125-2 through the measurement light source 130.

Figure 1:
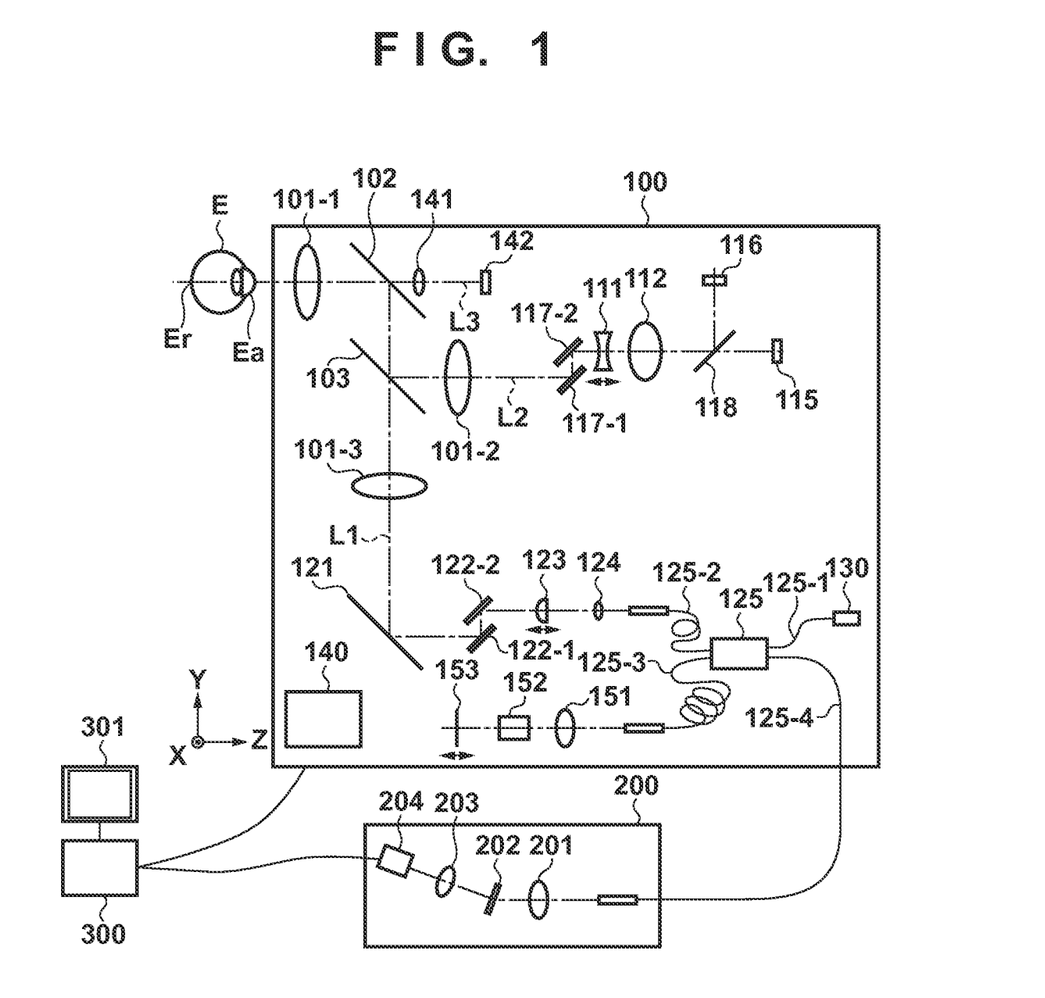
FIG. 1 is a view showing an example of the arrangement of an optical coherence tomography apparatus (ophthalmic apparatus) according to the first embodiment.

Referring to FIG. 1, although the optical path between the X scanner 122-1 and the Y scanner 122-2 looks as if it were formed within the drawing surface, the optical path is actually formed in a direction perpendicular to the drawing surface. The optical head unit 100 includes a head driving unit 140. The head driving unit 140 is constituted by three motors (not shown) and is configured to be able to move the optical head unit 100 in three-dimensional (X, Y, Z) directions relative to the eye E. This makes it possible to align the optical head unit 100 with eye E.

The arrangements of the optical path from the measurement light source 130, reference optical system, and spectroscope 200 will be described next. The light source 130, an optical coupler 125, optical fibers 125-1 to 125-4, a lens 151, a dispersion compensation glass 152, a mirror 153, and the spectroscope 200 constitute a Michelson interferometer system. The optical fibers 125-1 to 125-4 are single-mode optical fibers, which are connected to the optical coupler 125 so as to be integrated.

The light emitted from the light source 130 is divided into measurement light which emerges to the optical fiber 125-2 through the optical fiber 125-1 and the optical coupler 125 and reference light which emerges to the optical fiber 125-3. The measurement light enters the fundus Er of the eye E as an observation target through the above OCT optical system optical path and reaches the optical coupler 125 through the same optical path by reflection and scattering by the retina.

On the other hand, reference light reaches and is reflected by the mirror 153 through the optical fiber 125-3, the lens 151, and the dispersion compensation glass 152 inserted to match the dispersion of measurement light with that of reference light. This light then returns along the same optical path and reaches the optical coupler 125. The optical coupler 125 combines measurement light and reference light to form interference light. In this case, interference occurs when the optical path length of the measurement light becomes almost equal to that of the reference light. A motor and driving mechanism (not shown) hold the mirror 153 so as to adjust its position in the optical axis direction, thereby matching the optical path length of measurement light, which changes depending on the eye E, with that of reference light. Interference light is guided to the spectrometer or spectroscope 200 through the optical fiber 125-4.

The spectroscope 200 is constituted by a lens 201, a diffraction grating 202, a lens 203, and a line sensor 204. The interference light emerging from the optical fiber 125-4 is collimated through the lens 201 and then spectroscoped by the diffraction grating 202. The lens 203 forms the resultant light into an image on the line sensor 204.

The surroundings of the measurement light source 130 will be described next. The measurement light source 130 is an SLD (Super Luminescent Diode) which is a typical low-coherent light source. The SLD emits light having a center wavelength of 855 nm and a wavelength bandwidth of about 100 nm. In this case, a band width influences the resolution of an obtained tomographic image in the optical axis direction, and hence is an important parameter. In this case, an SLD is selected as the type of light source to be used. However, it is possible to use an ASE (Amplified Spontaneous Emission) light source or the like as long as it can emit low-coherent light. In consideration of measurement of the eye, the wavelength of near-infrared light is suitable as the center wavelength of light to be used. In addition, the center wavelength influences the resolution of an obtained tomographic image in the lateral direction, and hence is preferably as short as possible. For the above two reasons, the center wavelength is set to 855 nm.

This embodiment uses a Michelson interferometer as an interferometer. However, the embodiment may use a Mach-Zehnder interferometer. It is preferable to use a Mach-Zehnder interferometer if the light amount difference between measurement light and reference light is large, whereas it is preferable to use a Michelson interferometer if the light amount difference is small.

Arrangement of Control Unit 300

The control unit 300 is connected to the respective units of the optical head unit 100 and spectroscope 200. More specifically, the control unit 300 is connected to the infrared CCD 142 in the optical head unit 100 and is configured to be able to generate an observation image of the anterior ocular segment Ea of the eye E. The control unit 300 is also connected to the APD 115 in the optical head unit 100 and is configured to be able to generate an observation image of the fundus Er of the eye E. In addition, the control unit 300 is connected to the head driving unit 140 in the optical head unit 100 and is configured to be able to three-dimensionally drive the optical head unit 100 relative to the eye E.

The control unit 300 is also connected to the line sensor 204 of the spectroscope 200. This makes it possible to acquire a measurement signal whose wavelength is decomposed by the spectroscope 200 and to also generate a tomographic image of the eye E based on the measurement signal.

A monitor 301 connected to the control unit 300 can display the generated anterior ocular segment observation image, fundus observation image, and tomographic image of the eye E.

Method of Aligning Eye E

Figure 2:
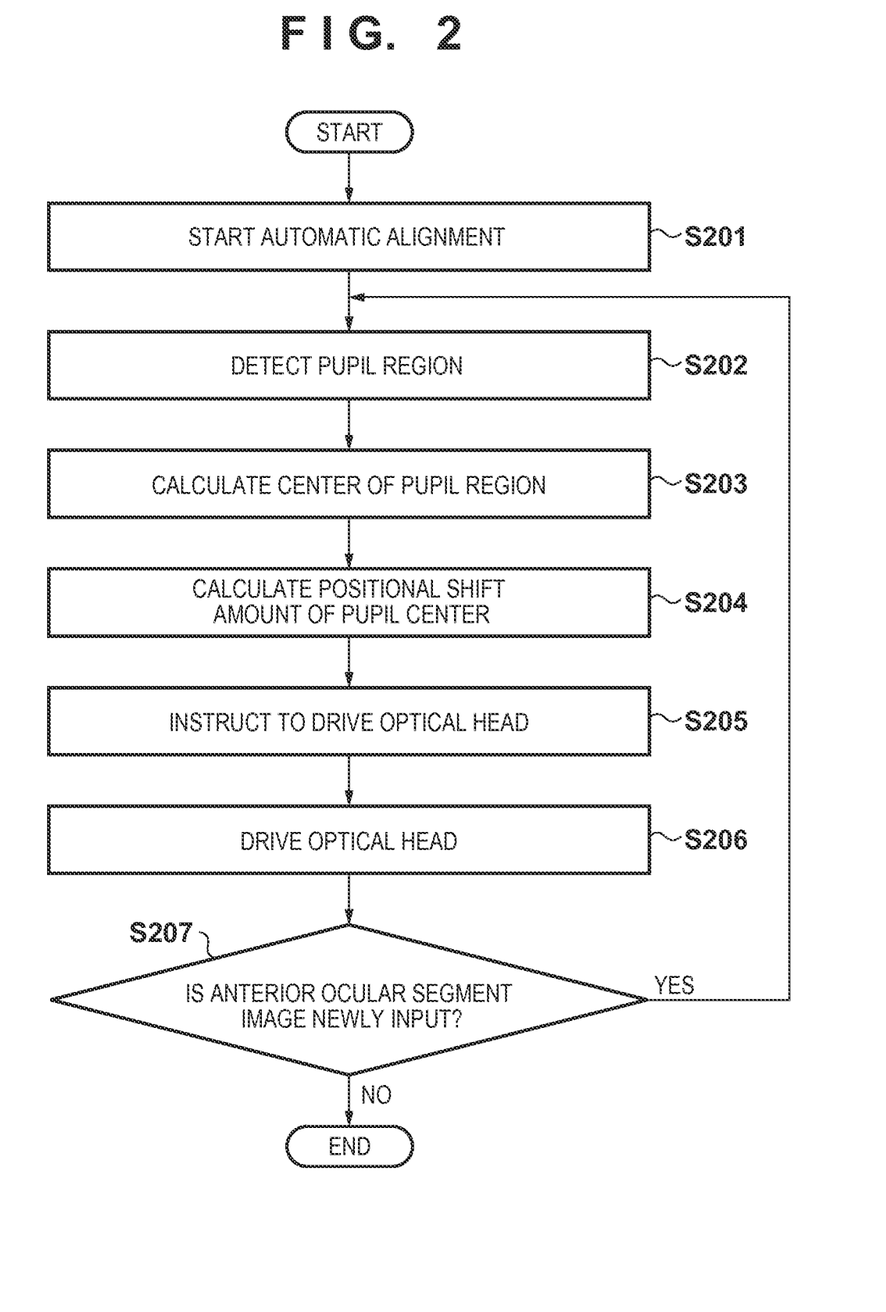
FIG. 2 is a flowchart snowing a procedure for automatic alignment processing according to the first embodiment.

A method of aligning the eye E by using the optical coherence tomography apparatus according to this embodiment will be described next with reference to FIG. 2. Before imaging operation, the examiner places the object to be examined in front of the apparatus, for example by seating a person to be examined take a seat in front of the apparatus.

In step S201, the control unit 300 starts automatic alignment upon operation on a switch (not shown) by the examiner. In step S202, the control unit 300 functions as an anterior ocular segment image acquisition unit. Upon starting automatic alignment, the control unit 300 periodically acquires and analyzes an anterior ocular segment image from the infrared CCD 142. More specifically, the control unit 300 detects a pupil region in an input anterior ocular segment image.

In step S203, the control unit 300 calculates the central position of the detected pupil-region. In step S204, the control unit 300 calculates the displacement amount (positional displacement) between the central position of the detected pupil region and the central position of the anterior ocular segment image. The optical coherence tomography apparatus according to this embodiment is configured such that the center of an anterior ocular segment image coincides with the optical axis of the objective lens 101-1. The display amount calculated in step S204 represents the positional displacement between the eye E and the measurement optical axis. In addition, a positional displacement may include not only a displacement amount but also a displacement direction.

In step S205, the control unit 300 issues an instruction to the head driving unit 140 to move the optical head unit 100 in accordance with the positional displacement calculated in step S204. In step S206, the head driving unit 140 drives three motors (not shown) to move the position of the optical head unit 100 in three-dimensional (X, Y, Z) directions relative to the eye E. As a result of this movement, the position of the optical axis of the lens 101-1 mounted on the optical head unit 100 is corrected so as to approach the position of the pupil center of the anterior ocular segment Ea of the eye E.

In step S207, upon moving the optical head unit 100, the control unit 300 determines whether a new anterior ocular segment image is input from the infrared CCD 142. If the control unit 300 determines that a new anterior ocular segment image is input (YES in step S207), the process returns to step S202. If the control unit 300 determines that no new anterior ocular segment is input (NO in step S207), the control unit 300 terminates the processing.

With this series of alignment operations, the optical axis position of the objective lens 101-1 always moves to track the position of the pupil center of the anterior ocular segment Ea of the eye E. Even if the line-of-sight direction of the eye E changes, this automatic alignment operation makes the optical axis of the objective lens 101-1 track the pupil center of the anterior ocular segment Ea after the change in line of sight. This makes it possible to stably capture a tomographic image by irradiating the fundus Er with the measurement light beam emitted from the measurement light source 130 without being shielded by the pupil.

This series of automatic alignment operations continues until the apparatus starts scanning measurement light on the fundus region Er of the eye E to record a tomographic image of the fundus region Er of the eye E.

Note that this embodiment performs automatic alignment for the optical system relative to an eye to be examined based on the anterior ocular segment image obtained by the infrared CCD. However, the embodiment may execute this operation by using another method. For example, it is possible to perform automatic alignment in three-dimensional (X, Y, Z) directions by projecting an alignment index on the anterior ocular segment of the eye to be examined and detecting reflected light.

Fundus Tracking Method

Upon starting the above automatic alignment operation, the control unit 300 starts the operation of acquiring a two-dimensional observation image (fundus image) of the fundus Er through the optical path L2. More specifically, the control unit 300 starts acquiring reflected light from the fundus Er which is input from the APD 115. The X scanner 117-1 and the Y scanner 117-2 functioning as the scanning unit for tomographic image acquisition continuously scans reflected light from the fundus Er on the fundus Er two-dimensionally. It is therefore possible to periodically obtain a fundus observation image by periodically combining reflected light input from the APD 115 (fundus image acquisition processing).

The control unit 300 then starts fundus tracking operation based on periodically acquired fundus observation images. When starting fundus tracking, the control unit 300 detects the movement (positional displacement) of the fundus Er by using a fundus reference image as a previously acquired fundus observation image and a fundus target image as a current fundus observation image. The control unit 300 controls the X scanner 122-1 and the Y scanner 122-2, which function as a scanning unit for tomographic image acquisition, in accordance with the calculated movement (positional displacement) of the fundus Er to change and correct the acquisition position (scan position) of a tomographic image so as to always irradiate the same region on the fundus Er with measurement light through the optical path L1.

Figure 3:
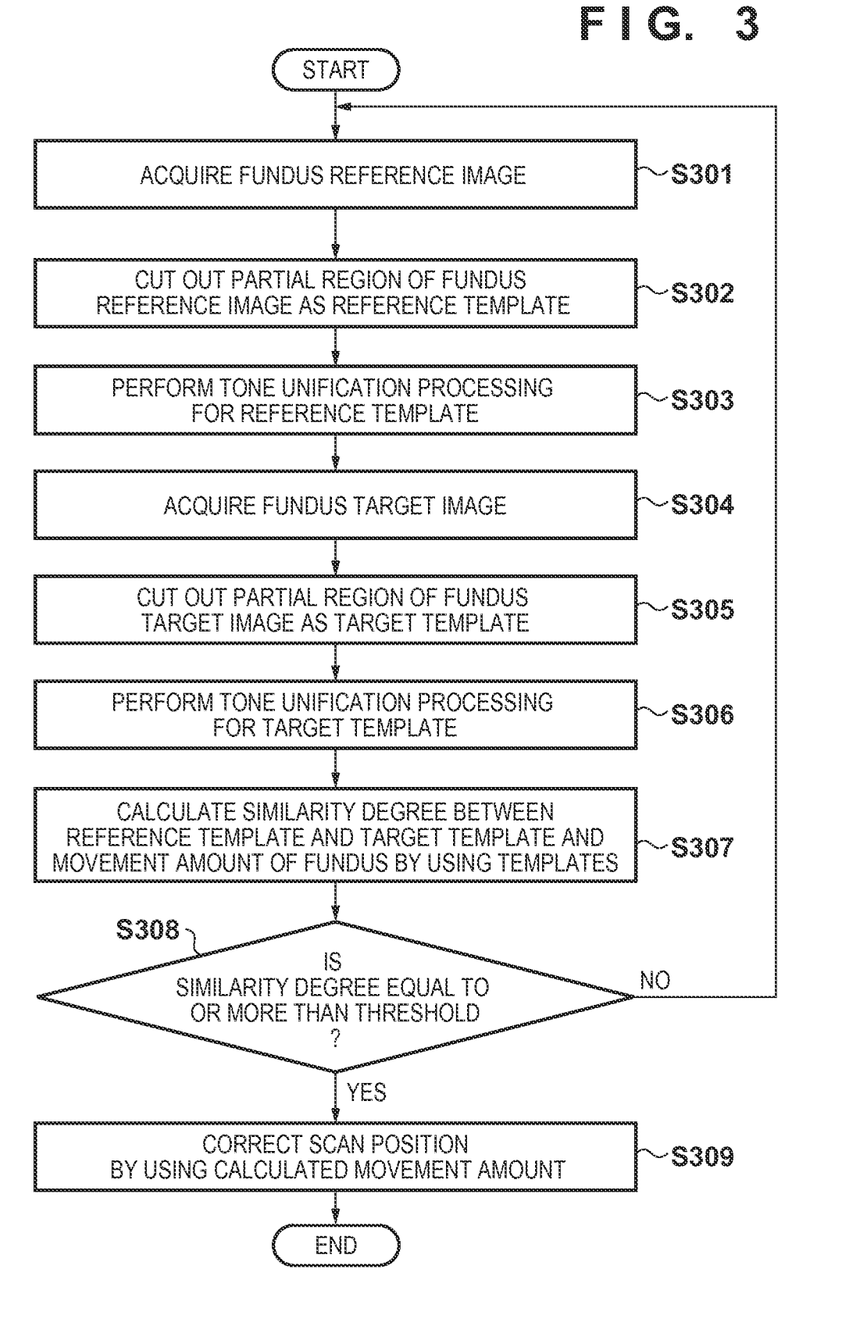
FIG. 3 is a flowchart showing a procedure for fundus tracking processing according to the first embodiment.

The details of the fundus tracking method according to the first embodiment will be described below with reference to the flowchart of FIG. 3, in which when irradiating the fundus region Er of the eye E with measurement light for the observation of the state of the eye E, the apparatus corrects the shift of measurement light irradiation position which occurs accompanying the movement of the eye E.

Figure 4:
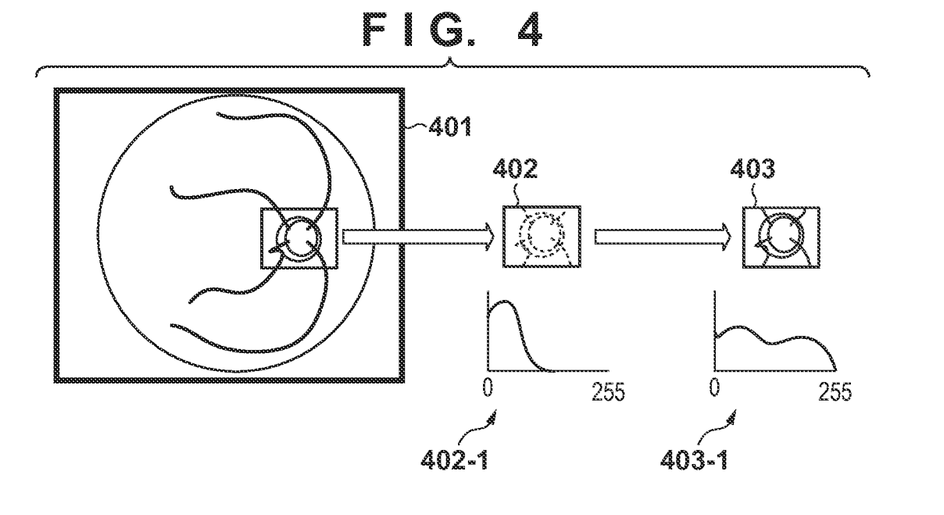
FIG. 4 is a view showing an example of the generation of a template including tone unification processing according to the first embodiment.

In step S301, the control unit 300 acquires a fundus reference image 401 (first fundus image), as shown in FIG. 4.

In step S302, the control unit 300 cuts out (extracts) a partial region (first characteristic region) of the fundus reference image 401 as a reference template 402. The reference template 402 has a luminance distribution indicated by a histogram 402-1. In the example shown in FIG. 4, a partial region of the fundus reference image 401 is a region including the optic papilla. However, this region is not necessarily limited to the optic papilla region. The region may be another blood vessel region.

In step S303, the control unit 300 performs luminance conversion by performing processing for enhancing the contrast of the reference template 402 (for example, tone conversion processing or tone unification processing), thereby acquiring a reference template 403 (an image which corresponds to the first characteristic region) (first generation processing).

The reference template 403 after tone unification processing has the luminance distribution of a histogram 403-1. That is, the luminance distribution and contrast of this temperate have been improved. Note that the contrast may be further improved by using an edge detection filter.

In step S304, the control unit 300 acquires a fundus target image (second fundus image) 5001.

In step S305, the control unit 300 cuts out a partial region (second characteristic region) of the fundus target image as a target template (not shown) based on the cut position and size of the reference template 403.

Figure 5:
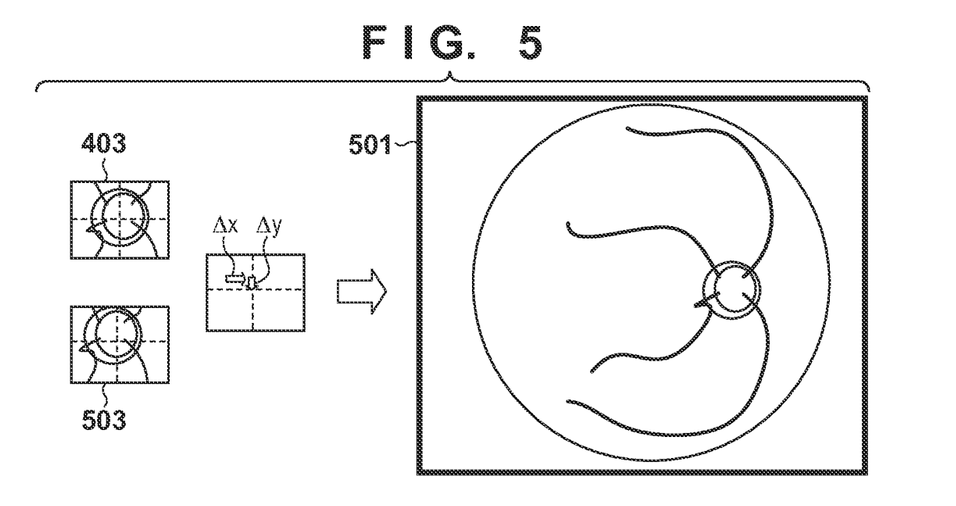
FIG. 5 is a view showing an example of fundus tracking operation including template matching processing according to the first embodiment.

In step S306, the control unit 300 performs luminance conversion by performing tone unification processing for the target template cut out in step S305, and acquires a target template 503 (an image which corresponds to the second characteristic region) (second generation processing), as shown in FIG. 5.

In step S307, the control unit 300 calculates the movement amount (positional displacement) of the fundus Er by calculating the displacement amount and/or displacement direction ($\Delta x$, $\Delta y$) in two-dimensional (X, Y) directions using the reference template 403 and the target template 503. The control unit 300 calculates the similarity degree between the reference template 403 and the target template 503 (similarity degree calculation processing). The similarity degree can be calculated, for example, as the ratio of the number of pixels of an overlapping region to the total number of pixels of the templates when the reference template 403 is matched with the target template 503. Alternatively, the similarity degree may be calculated as the degree of correlation between the luminance distribution of the histogram 403-1 of the reference template 403 and the luminance distribution (not shown) of the histogram of the target template 503. In addition, the similarity degree may be a value (for example, a cross-correlation coefficient) concerning the cross-correlation obtained from the reference template 403 and the target template 503.

In step S308, the control unit 300 determines whether the similarity degree calculated in step S307 is equal to or more than a threshold (i.e. that it is not less than the threshold). If the control unit 300 determines that the similarity degree is equal to or more than the threshold (YES in step S308), the process advances to step S309. If the control unit 300 determines that the similarity degree is less than the threshold (NO in step S308), the process returns to step S301.

Note that even the execution of tone unification processing may not lead to sufficient accuracy of fundus tracking due to the influences of eyelid and eyelashes of the eye E. On the assumption of such a case, the apparatus may calculate, as a similarity degree, a value concerning the cross-correlation (for example, a cross-correlation coefficient) obtained from the reference template 403 and the target template 503 and determine a decrease in similarity degree. If, for example, when the templates perfectly match with each other, the corresponding similarity degree is 1. In this case, if the maximum value of a cross-correlation coefficient is equal to or less than a similarity degree of 0.4 (threshold), the apparatus may determine that the accuracy of fundus tracking is insufficient. Although the threshold is set to a similarity degree of 0.4 or less, the threshold may be set to an arbitrary value according to an empirical rule.

In step S309, the control unit 300 controls the X scanner 122-1 and the Y scanner 122-2 in accordance with the calculated movement amount (positional displacement) of the fundus Er to change and correct the acquisition position (scan position) of a tomographic image so as to always irradiate the same region on the fundus Er with measurement light through the optical path L1 (position correction processing).

With the series of fundus tracking operations described above, the irradiation position of measurement light emitted from the light source 130 onto the fundus Er always moves to track the movement of the fundus Er. This allows stable tomography. This series of fundus tracking operations continues until the end of examination on the eye E.

As described above, the optical coherence tomography apparatus according to this embodiment can obtain preferable tomographic images with little deformation by performing fundus tracking using a template having undergone luminance conversion by tone unification processing and correcting the scan position based on the tracking result.

Note that this embodiment performs fundus tracking using fundus observation images by a point scanning type SLO designed to perform two-dimensional scanning using two scanners. However, the embodiment may execute this operation by using another method. For example, the embodiment may use a line scanning type designed to scan a line beam one-dimensionally. In addition, the embodiment can perform fundus tracking by using a two-dimensional fundus observation image obtained by using a combination of: i) infrared, light capable of irradiating the fundus in a wide range; and ii) an infrared CCD. It is also possible to perform fundus tracking by projecting an arbitrary pattern formed by a light source and using reflected light from the fundus. Furthermore, the scanning type of an OCT optical system can also use the same method as that used by the SLO optical system, and the embodiment can also use a full field type designed to perform imaging collectively by using an area sensor without scanning.

Method of Capturing Tomographic Image

A method of capturing a tomographic image by using the optical coherence tomography apparatus according to this embodiment will be described next. The examiner starts imaging by operating a switch (not shown) on the control unit 300. The control unit 300 starts generating a tomographic image for recording based on the interference light periodically output from the line sensor 204 in accordance with an instruction to start imaging.

In this case, the interference light output from the line sensor 204 is a signal for each frequency spectroscoped by the diffraction grating 202. The control unit 300 generates information in the depth direction at a given point on the fundus Er by performing FFT (Fast Fourier Transform) for a signal from the line sensor 204. The generation of information in the depth direction at a given point on the fundus Er will be referred to as an A scan.

It is possible to control the scan of measurement light, with which the fundus Er is irradiated, on the fundus Er by driving/controlling one or both of the X scanner 122-1 and the Y scanner 122-2.

The control unit 300 combines a series of A scans acquired during one scan along this controlled locus into one two-dimensional image to generate a tomographic image on the locus of the fundus Er.

The control unit 300 further repeats a scan along the locus described above a plurality of times by driving/controlling at least one of the X scanner 122-1 and the Y scanner 122-2. Repeating operation along the same locus a plurality of times can obtain a plurality of tomographic images on the locus of the fundus Er. For example, the control unit 300 iteratively executes scanning in the X direction by driving the X scanner 122-1 to generate a plurality of tomographic images on the same scanning line on the fundus Er. In addition, the control unit 300 can generate a plurality of tomographic images on the same circle on the fundus Er by iteratively executing an operation in a circular form by simultaneously driving the X scanner 122-1 and the Y scanner 122-2. The control unit 300 then generates one tomographic image with high image quality by averaging these tomographic images, and displays the image on the monitor 301.

Figure 6:
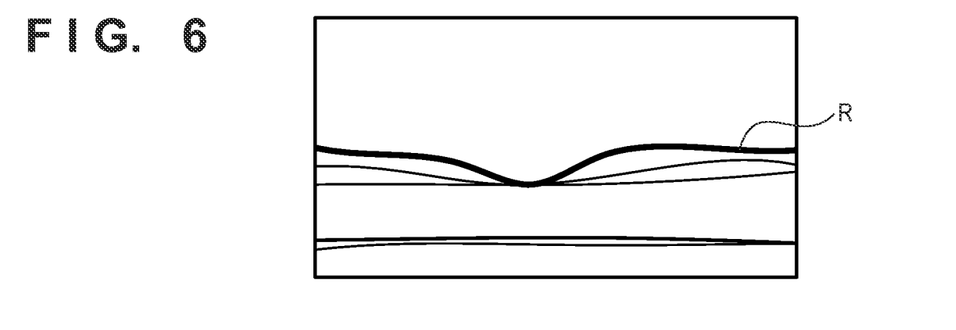
FIG. 6 is a view showing an example of a tomographic image captured by the optical coherence tomography apparatus according to the first embodiment.

On the other hand, the control unit 300 can also perform scanning a plurality of times while shifting the scan position along the locus described above in the X and Y directions by driving/controlling at least one of the X scanner 122-1 and the Y scanner 122-2. For example, performing scanning in the X direction while shifting the scan position in the Y direction at predetermined intervals will generate a plurality of tomographic images covering the entire rectangular region on the fundus Er. The control unit 300 then generates three-dimensional information of the fundus Er by combining a plurality of tomographic images, and displays the information on the monitor 301. FIG. 6 shows an example of the tomographic image obtained by imaging the anterior ocular segment Ea of the eye to be examined, with R representing the retina.

When acquiring a tomographic image for recording, this embodiment performs control to correct the scan position between the respective scans. However, the embodiment may execute control in the same manner when acquiring a tomographic image for observation. In this case, it is possible to reduce the distortion of the retina on a tomographic image for observation.

In addition, when acquiring a tomographic image for observation, the apparatus may correct the scan position upon detecting of the movement of the fundus Er instead of correcting the scan position between the respective scans. A tomographic image for observation is displayed as a real-time observation image. The display period of this image is very short. Furthermore, since no tomographic image for observation is used for diagnosis, some distortion of the retinal layer is tolerable.

Second Embodiment

Fundus Tracking Method

Figure 7:
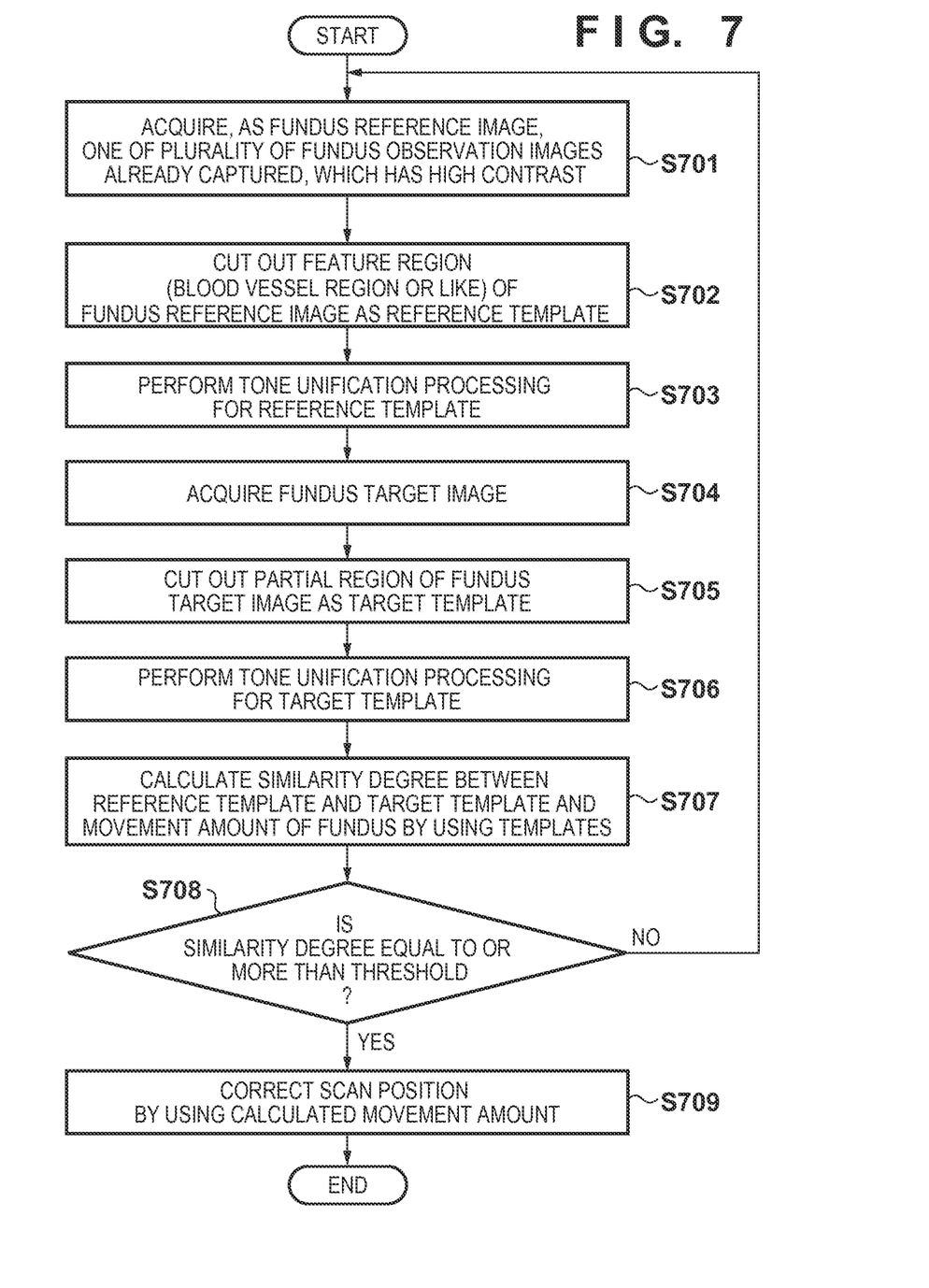
FIG. 7 is a flowchart showing a procedure for fundus tracking processing according to the second embodiment.

The details of a fundus tracking method according to the second embodiment will be described below with reference to the flowchart of FIG. 7, in which when irradiating a fundus region Er of an eye E to be examined with measurement light for the observation of the state of the eye E, the apparatus corrects the shift of measurement light irradiation position which occurs accompanying the movement, of the eye E.

A control unit 300 starts acquiring a two-dimensional observation image of the fundus Er of the eye to be examined through an optical path L2 in the same manner as in the first embodiment after the start of automatic alignment operation described above.

In step S701, the control unit 300 acquires, as a fundus reference image, one of a plurality of fundus observation images captured already, which has high contrast. If a fundus observation image is out of focus, the apparatus may newly acquire a fundus reference image after performing focusing processing for fundus observation by driving a lens 111 (focus lens).

In step S702, the control unit 300 selects a characteristic region such as a blood vessel region from the fundus reference image acquired in step S701, decides a cut position and a cut size, and cuts out a reference template 401 as shown in FIG. 4. Since each of processes in steps S703 to S709 is the same as that in steps S303 to S309, a description of them will be omitted.

Note that if the similarity degree is less than the threshold in step S708, a trouble may occur in cutting out a template. In general, a template is cut out in a narrowest possible range to speed up fundus tracking. However, insufficient focus, eye disease, or the like sometimes decreases the similarity degree, and hence the value of the similarity degree is improved sometimes by reexamining the cut range of a template. That is, if the similarity degree is less than a threshold, the cut size of a template is changed to a larger size when a template is to be generated again afterward. The maximum size of a template to be cut out is decided based on the fundus tracking allowable time.

As has been described above, this embodiment acquires, as a fundus reference image, one of fundus observation images of the eye to be examined, which has high contrast, and performs tone unification processing, thereby further increasing the contrast of a characteristic region (blood vessel region or the like). This makes it possible to perform accurate fundus tracking. It is therefore possible to reduce the influence of the movement of the eye on a captured tomographic image and obtain an image with high image quality. In addition, even if the eye to be examined moves during capturing of an image serving as a fundus tracking target, it is possible to reduce the influences of the vignetting of an imaging light beam at the pupil of the eye to be examined due to the decentering of the imaging optical axis and illuminance unevenness due to the tilt of the eye.

Other Embodiments

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-190617 filed on Aug. 30, 2012, which is hereby incorporated by reference herein in its entirety.

What is claimed is:

1. An ophthalmic apparatus comprising:
a fundus image acquisition unit configured to acquire a first fundus image of an eye and a second fundus image of the eye which is captured at a time different from that of the first fundus image;
a first generation unit configured to generate, by performing processing of enhancing contrast of a first characteristic region of a part of the first fundus image, an image which corresponds to the first characteristic region;
a second generation unit configured to generate, by performing processing of enhancing contrast of a second characteristic region of a part of the second fundus image which corresponds to the first characteristic region, an image which corresponds to the second characteristic region; and
a position correction unit configured to correct an acquisition position of a tomographic image of the eye based on a positional displacement between the image which corresponds to the first characteristic region and the image which corresponds to the second characteristic region.

2. The ophthalmic apparatus according to claim 1, further comprising:
a similarity degree calculation unit configured to calculate a similarity degree between the image which corresponds to the first characteristic region and the image which corresponds to the second characteristic region; and
a determination unit configured to determine whether the similarity degree is not less than a threshold,
wherein if said determination unit determines that the similarity degree is not less than the threshold, said position correction unit corrects the acquisition position of the tomographic image.

3. The ophthalmic apparatus according to claim 2, wherein said similarity degree calculation unit calculates, as the similarity degree, a value concerning a cross-correlation between the image which corresponds to the first characteristic region and the image which corresponds to the second characteristic region.

4. The ophthalmic apparatus according to claim 3, wherein said first generation unit and said second generation unit respectively generate the image which corresponds to the first characteristic region and the image which corresponds to the second characteristic region again if said determination unit determines that the similarity degree is less than the threshold.

5. The ophthalmic apparatus according to claim 4, wherein said first generation unit and said second generation unit respectively generate the image which corresponds to the first characteristic region and the image which corresponds to the second characteristic region again by changing cut sizes of the first characteristic region and the second characteristic region to larger sizes.

6. The ophthalmic apparatus according to claim 1, further comprising a selection unit configured to select, as the first fundus image, one of a plurality of fundus images of the eye captured by said fundus image acquisition unit at different times, which has higher contrast than other fundus images.

7. The ophthalmic apparatus according to claim 1, wherein the first characteristic region and the second characteristic region are blood vessel regions.

8. The ophthalmic apparatus according to claim 1, further comprising:
   a focus lens which captures the fundus image; and
   a focus leans driving unit configured to perform focusing processing by driving said focus lens,
   wherein said first generation unit and said second generation unit respectively generate the image which corresponds to the first characteristic region and the image which corresponds to the second characteristic region after execution of the focusing processing.

9. The ophthalmic apparatus according to claim 1, wherein the processing of enhancing the contrast comprises tone conversion processing of converting tones of the first characteristic region and the second characteristic region.

10. The ophthalmic apparatus according to claim 1, wherein the processing of enhancing the contrast comprises tone unification processing of unifying tones of the first characteristic region and the second characteristic region.

11. The ophthalmic apparatus according to claim 1, further comprising scanning unit for fundus image acquisition and scanning unit for tomographic image acquisition, configured to scan light emitted from a light source on an eye,
   wherein said fundus image acquisition unit acquires the first fundus image and the second fundus image based on reflected light from the eye based on light scanned by said scanning unit for fundus image acquisition, and
   said position correction unit corrects an acquisition position of a tomographic image of the eye by correcting a scan position of said scanning unit for tomographic image acquisition based on a positional displacement between the image which corresponds to the second characteristic region and the image which corresponds to the second characteristic region.

12. A method of controlling an ophthalmic apparatus comprising the steps of:
   a fundus image acquisition step of acquiring a first fundus image of an eye and a second fundus image of the eye which is captured at a time different from that of the first fundus image;
   a first generation step of generating, by performing processing of enhancing contrast of a first characteristic region of a part of the first fundus image, an image which corresponds to the first characteristic region;
   a second generation step of generating, by performing processing of enhancing contrast of a second characteristic region of a part of the second fundus image which corresponds to the first characteristic region, an image which corresponds to the second characteristic region; and
   a position correction step of correcting an acquisition position of a tomographic image of the eye based on a positional displacement between the image which corresponds to the first characteristic region and the image which corresponds to the second characteristic region.

13. A non-transitory computer-readable storage medium storing a computer program for causing a computer to function as each unit of an ophthalmic apparatus defined in claim 1.

* * * * *